US008166479B2

(12) United States Patent
Roberts et al.

(10) Patent No.: US 8,166,479 B2
(45) Date of Patent: Apr. 24, 2012

(54) OPTIMIZING DATA ANALYSIS THROUGH DIRECTIONAL DEPENDENCIES OF A GRAPH INCLUDING PLURALITY OF NODES AND ATTRIBUTING THREADING MODELS AND SETTING STATUS TO EACH OF THE NODES

(75) Inventors: David Roberts, Sheffield (GB); Tony Burpee, Bolsover (GB)

(73) Assignee: Softlife Projects Limited as Applied Cytometry Systems, Sheffield (GB)

( * ) Notice: Subject to any disclaimer, the term of this patent is extended or adjusted under 35 U.S.C. 154(b) by 972 days.

(21) Appl. No.: 12/147,312

(22) Filed: Jun. 26, 2008

(65) Prior Publication Data

US 2009/0007127 A1 Jan. 1, 2009

Related U.S. Application Data

(60) Provisional application No. 60/946,381, filed on Jun. 26, 2007.

(51) Int. Cl.
*G06F 9/46* (2006.01)
(52) U.S. Cl. ........................................ 718/100
(58) Field of Classification Search ............. 718/106
See application file for complete search history.

(56) References Cited

U.S. PATENT DOCUMENTS

| | | | |
|---|---|---|---|
| 3,662,401 A * | 5/1972 | Collins et al. | 718/103 |
| 5,675,517 A | 10/1997 | Stokdijk | |
| 6,044,394 A | 3/2000 | Cadden et al. | |
| 6,189,141 B1 | 2/2001 | Benitez et al. | |
| 6,499,023 B1 * | 12/2002 | Dong et al. | 706/46 |
| 6,553,355 B1 * | 4/2003 | Arnoux et al. | 706/13 |
| 6,748,518 B1 | 6/2004 | Guthrie et al. | |
| 6,954,722 B2 | 10/2005 | Parks et al. | |
| 7,024,316 B1 | 4/2006 | Ellison et al. | |
| 7,089,557 B2 | 8/2006 | Lee | |
| 7,321,983 B2 | 1/2008 | Amarnath et al. | |

(Continued)

FOREIGN PATENT DOCUMENTS

EP 0536946 A2 4/1993

(Continued)

OTHER PUBLICATIONS

Yu-Kwong Kwok & Ishfaq Ahmad, "Static Scheduling Algorithms for Allocating Directed Task Graphs to Multiprocessors," ACM Computing Surveys, vol. 31, No. 4, Dec. 1999, pp. 407-471.

(Continued)

*Primary Examiner* — Meng An
*Assistant Examiner* — Wissam Rashid
(74) *Attorney, Agent, or Firm* — Allen J. Moss; Squire Sanders (US) LLP

(57) ABSTRACT

There is provided an adaptive semi-synchronous parallel processing system and method, which may be adapted to various data analysis applications such as flow cytometry systems. By identifying the relationship and memory dependencies between tasks that are necessary to complete an analysis, it is possible to significantly reduce the analysis processing time by selectively executing tasks after careful assignment of tasks to one or more processor queues, where the queue assignment is based on an optimal execution strategy. Further strategies are disclosed to address optimal processing once a task undergoes computation by a computational element in a multiprocessor system. Also disclosed is a technique to perform fluorescence compensation to correct spectral overlap between different detectors in a flow cytometry system due to emission characteristics of various fluorescent dyes.

40 Claims, 10 Drawing Sheets

U.S. PATENT DOCUMENTS

| | | |
|---|---|---|
| 2003/0078703 A1 | 4/2003 | Potts |
| 2005/0081107 A1 | 4/2005 | DeWitt |
| 2006/0015291 A1 | 1/2006 | Parks |
| 2006/0059484 A1 | 3/2006 | Selvaggi |
| 2006/0168571 A1 | 7/2006 | Ghiasi |
| 2006/0294499 A1 | 12/2006 | Shim |
| 2007/0038987 A1 | 2/2007 | Ohara et al. |
| 2007/0143759 A1 | 6/2007 | Ozgur et al. |

FOREIGN PATENT DOCUMENTS

| | | |
|---|---|---|
| JP | 05150981 | 6/1993 |
| JP | 1175355 | 7/1999 |
| JP | 11175357 | 7/1999 |
| WO | 9634270 | 10/1996 |

OTHER PUBLICATIONS

Yu-Kwong Kwok & Ishfaq Ahmad, "Dynamic Critical-Patent Scheduling: An Effective Technique for Allocating Task Graphs to Multi-processors," IEEE Transactions on Parallel and Distributed Systems, vol. 7, No. 5, May 1996, pp. 506-521.

\* cited by examiner

OPTIMIZING DATA ANALYSIS THROUGH DIRECTIONAL DEPENDENCIES OF A GRAPH INCLUDING PLURALITY OF NODES AND ATTRIBUTING THREADING MODELS AND SETTING STATUS TO EACH OF THE NODES

CROSS REFERENCE TO RELATED APPLICATIONS

This application claims full benefit of and priority to U.S. Provisional Patent Application No. 60/946,381 filed Jun. 26, 2007 titled, "Method, System, and Apparatus for Optimizing Data Analysis" the disclosure of which is fully incorporated herein by reference for all purposes.

DESCRIPTION OF THE INVENTION

1. Field of the Invention

The present invention relates to systems and methods and for optimizing computing resources, and more particularly, to systems and methods for optimizing processing of tasks within a parallel computing architecture.

2. Background of the Invention

In the ever-expanding quest for increased computational power, vector or parallel computer processor architectures have been used for many years to allow tasks to be executed concurrently, thereby increasing overall computational speed. Early vector processors have evolved to massively parallel systems such as the IBM Blue Gene/L, which in one configuration has 65,536 computational nodes distributed among 64 cabinets delivering a theoretical peak performance of 360 terra-FLOPS. More recently, integrated circuit microprocessors have been developed that include a plurality of processor cores, making parallel computing possible even on modest physical scales. Each of the processor cores can perform operations interdependently from another processor core and can perform operations in parallel with another processor core. For example, Intel Pentium processors have offered dual core configurations, and quad core implementations are soon planned for market introduction.

While multi-processor hardware continues to advance, methods and systems need to be developed to effectively partition tasks between the processors in such a way to maximize the performance of the entire system. Without such intelligent task management, processors available in the system may become underutilized as one or more processors sit idle while others perform significantly more work. Such efficient use of resources is needed particularly in an environment that requires analysis of large amounts of data originating from a variety of sources.

SUMMARY OF THE INVENTION

It is an object of the invention to solve various problems in the art, and at least those problems referenced in the background section, above. Therefore, are provided an adaptive semi-synchronous parallel processing systems and methods, which may be adapted to various data analysis applications such as flow cytometry systems. By identifying the relationship and memory dependencies between tasks that are necessary to complete an analysis, it is possible to significantly reduce the analysis processing time by selectively executing tasks after careful assignment of tasks to one or more processor queues, where the queue assignment is based on an optimal execution strategy. Further strategies are disclosed to address optimal processing once a task undergoes computation by a computational element in a multiprocessor system. Also disclosed is a technique to perform fluorescence compensation to correct spectral overlap between different detectors in a flow cytometry system due to emission characteristics of various fluorescent dyes.

When data requires analysis by automated methods, the analysis can be decomposed into a set of operations (such as tasks) that need to be performed on the data to achieve the desired results. As some of the operations are predicated on the results of other operations, there is a dependency between the operations; some operations cannot be processed until other operations have completed processing.

When all of the necessary operations are logically connected together in a manner that represents dependencies between operations, a directed graph results, with the operations represented by vertices (nodes), and the dependencies represented by the directed edges of the graph. By representing the analysis as a directed graph, algorithms can be applied to establish the a preferred order of processing that should be applied to the operations to reduce processing times and/or obtain optimal utilization of resources such as processor cores in a multiprocessor system.

Various data attributes may be associated with a data structure representing nodes, for instance, example attributes may include blocking status (e.g. "blocked" or "unblocked"), node generation (e.g. an ordinal number such as "1," "2," "3," and so on), vertex count (e.g. an ordinal number), processing states (e.g. "clean" or "dirty") or any other suitable information. These attributes are utilized by embodiments of the present invention to partition the graph into meaningful subsets where processing can be optimized by addressing certain node subsets of the graph in temporal- or location-based (e.g. memory-based) relationships to one another. Likewise, the graph may also be partitioned so that if only one operation needs to be performed, the corresponding nodes (or operations) from which it depends may be updated so that the relevant operation may produce meaningful and up-to-date results without having to process every operation or task defined within the graph.

A blocked or blocking vertex is a vertex that cannot be computed until all its input data is available. An example would be an auto region in a display that adjusts its position to be an upper percentile of a histogram. This operation normally cannot execute until all the histogram is built with all input data. As it may be desired to incrementally calculate the graph with data as it comes in from an asynchronous source (e.g. loading a file from disk, or an acquisition from an instrument), the difference between blocking and non blocking vertices should be distinguished and the nodes appropriately partitioned. Any vertex that depends on a blocking vertex is within the blocking set. The blocking attribute then propagates down the graph's edges designating vertices that depend upon the blocked vertex to also be in a blocked state.

Using graph algorithms, the partitioned vertices are sorted into generations. The first generation includes is vertices that have no dependencies; the second generation includes vertices that depend upon the first generation, and so on. In cases where a vertex depends on multiple parent vertices, the vertex generation is determined to be the highest generation of its parent vertices plus one. In one embodiment, calculation of the generations is performed by using a shortest paths algorithm.

To maximize the use of processor resources while maintaining lock safety, each vertex may include the designation of a threading model under which it may execute. In one embodiment, for each generation of vertices, the generations are partitioned into the desired set of threading models. In one embodiment, the threading models may include "Parallel," "Strip-mine," and "Do Not Thread" models. Parallel threading treats the set of vertices as a queue of tasks; a thread pool consumes the tasks within the queue. Once a thread has completed a task, it fetches the next available task from the queue.

Strip-mine threading splits data into a series of data sections. Threads from a thread pool consume a data section and perform all tasks within the set of strip-mined tasks on that data section. Once the thread has performed all tasks on a data section, it fetches the next available data section. One of the advantages of this method is that where multiple tasks within a generation are using the same data, the data is more likely to be immediately available in a processor's cache memory. For tasks that produce output data with a 1 to 1 correspondence with an event, it also eliminates or substantially reduces the need to use a lock to protect data access.

Likewise, there are situations where asynchronous or non-coherent processing is undesirable. "Do Not Thread" threading results in an approach where tasks are sequentially executed by the thread that executes the scheduling function.

In an embodiment, execution of the graph is undertaken by processing non-blocking nodes, followed by processing of blocking nodes. After tasks corresponding to nodes in the graph have been processed, the node attributes may be appropriately updated such as identifying them as "clean" or "processed."

An embodiment provides for a method for processing data that comprises: defining a plurality of tasks requiring execution; identifying one or more dependencies for each respective task of the plurality of tasks, the one or more dependencies comprising at least one of a resource dependency and a memory dependency; determining dependencies between for each respective task of the plurality of tasks wherein the dependencies include directional dependencies; creating a directed graph; and analyzing the directed graph to assign execution of tasks to a plurality of processors to maximize computational efficiency. The directed graph may includes a plurality of nodes, the nodes respectively corresponding to the plurality of tasks requiring execution; and a plurality of directed edges that respectively correspond to the directional dependencies, each of said directed edges originating from a node of the plurality of nodes and terminating on another node of the plurality of nodes.

One or more threading models may be attributed to each node of the plurality of nodes, and attributing a threading model to each node of the plurality of graphing may further include: assigning a parallel threading model to each said node where said node corresponds to a task that is independent, may operate in parallel, and has a non-blocked status; assigning a strip-mine threading model to each node in a collection of nodes that correspond to tasks that operate on common data; and assigning a non-threading model is assigned to nodes corresponding to tasks that must be executed sequentially. When nodes are assigned with a strip-mine threading model, each corresponding task may be iteratively computed for each data range associated with the task.

In an embodiment, attributing a strip-mine threading model comprises: partitioning a data set into a plurality of subsets, the size of each subset of the plurality of subsets chosen to be containable within a cache memory of predetermined size associated with a processor of the plurality of processors; allocating processing of a subset of the plurality of subsets to the processor; loading the subset of the plurality of subsets into the cache memory associated with the processor; executing a task utilizing the subset of the plurality of subsets; and indicating, by the processor, that another subset of the plurality of subsets may be allocated. Likewise, a branch prediction model may be assigned to a node of the plurality of nodes, the branch prediction model determined by an entropy characterization of data operated on by a function corresponding to the node.

Each node of the plurality of nodes may be assigned to one or more processing queues and tasks corresponding to each node assigned to the one or more processing queues are executed, and alternatively or in combination, each node of the plurality of nodes may be assigned to one or more processing queues based on the an identified memory dependency identified for that node. The consideration of memory dependency for making the assignment may include a desired cache level allocation.

Executing tasks assigned to the one or more processing queues may comprise: for each node of the plurality of nodes, determining whether the status of each node is blocked or un-blocked; and executing tasks corresponding to all non-blocked nodes of the plurality of nodes then executing tasks corresponding to all blocked nodes of the plurality of nodes. Execution of tasks corresponding to all blocked nodes of the plurality of graphing nodes may be repeated once data has become available.

Iteration provides for additional processing of embodiments of the present invention. In one implementation, the following steps are performed until all data is processed: setting status of all nodes of the plurality of nodes to processed or unprocessed status; when a task corresponding to a node of the plurality of nodes has been completely computed, setting status of the node to processed status; when data corresponding to a node of the plurality of nodes has been changed, setting status of the node to unprocessed status; and executing tasks corresponding to all unprocessed nodes of the plurality of nodes in accordance with respectively assigned threading models.

In another embodiment, a method is provided for optimizing utilization of processor resources comprising: determining a plurality of processing tasks required to perform a requested computation and obtaining from the plurality of processing tasks a set of task dependencies; determining, from the plurality of processing tasks and task dependencies, a blocking state for each of the plurality of processing tasks and setting the blocking state to blocked or non-blocked; instantiating a plurality of graphing nodes respectively representing the plurality of processing tasks wherein said plurality of nodes are initialized to a dirty state; defining a set of directed edges between pairs of individual nodes from the plurality of graphing nodes; counting references for each node of the plurality of graphing nodes; adding blocking attributes to one or more nodes of the plurality of graphing nodes; partitioning the plurality of graphing nodes into a blocked set and an non-blocked set; within each of the blocked set partition and the non-blocked set partition, assigning a generation number to each node of the plurality of graphing nodes; attributing a threading model to each node of the plurality of graphing nodes; assigning each node of the plurality of graphing nodes to one or more processing queues; and executing tasks assigned to the one or more processing queues. Further, the following steps may be performed until all data is processed: setting status of all nodes of the plurality of graphing nodes to clean or dirty status; when a task corresponding to a node of the plurality of graphing nodes has been completely computed, setting status of the node to clean status; when a data corresponding to a node of the plurality of graphing nodes has been changed, setting status of the node to dirty status; and executing all dirty nodes of the plurality of graphing nodes in accordance with respectively assigned threading models.

Directed edges may be defined between nodes in the graph, for instance, between pairs of nodes. Defining a set of directed edges between pairs of individual nodes from the plurality of graphing nodes may further comprise: adding a node reference to a node from the pair of individual nodes when the node has at least one of the set of directed edges directed to it; and not adding a node reference to a node from the pair of individual nodes when the node has at least one of the set of directed edges originating from the node.

In an embodiment, counting references for each node of the plurality of graphing nodes further comprises removing a node of the plurality of graphing nodes if the node has zero counted references. Also, assigning a generation number to each node of the plurality of graphing nodes may further comprise: assigning a node a generation number of 1 if the node has no directed edges terminating at the node; assigning a node a generation number of n if the node has a single directed edge terminating at the node that originated from a generation n−1 node; and if the node has multiple directed edges terminating at the node, assigning the node a generation number equal to 1 plus the maximum number of the generation number of the nodes from which the multiple directed edges originate.

In an additional embodiment, adding blocking attributes to one or more nodes of the plurality of graphing nodes may comprise: for each node of the plurality of graphing nodes, adding a blocking attribute to the node if: the node corresponds to a task with a blocked blocking state; or the node has a directed edge terminating at the node and the originating node of the directed edge has a blocked blocking state.

One or more threading models may be attributed to a node in any desired manner. For example, attributing a threading model to each node of the plurality of graphing nodes may comprise: assigning a parallel threading model to each said node where said node corresponds to a task that is independent, may operate in parallel, and has a non-blocked status; assigning a strip-mine threading model to each node in a collection of nodes that correspond to tasks that operate on common data; and assigning a non-threading model is assigned to nodes corresponding to tasks that must be executed sequentially. Further, a branch prediction model may be assigned to a node, the branch prediction model determined by an entropy characterization of data operated on by a function corresponding to the node. Threading models that include a strip-mine threading model may iteratively compute each corresponding task for each data range associated with the task.

Tasks may be executed by a blocked/blocking or non-blocked/non-blocking status indicator. In one embodiment, executing tasks assigned to the one or more processing queues further comprises executing tasks corresponding to all non-blocked nodes of the plurality of graphing nodes then executing tasks corresponding to all blocked nodes of the plurality of graphing nodes. Likewise, executing tasks corresponding to all non-blocked nodes of the plurality of graphing nodes further comprises repeating execution of tasks corresponding to all non-blocked nodes of the plurality of graphing nodes. In another embodiment, executing tasks corresponding to all blocked nodes of the plurality of graphing nodes further comprises repeating execution of tasks corresponding to all blocked nodes of the plurality of graphing nodes once data has become available.

Processing status may also be considered in accordance with various embodiments. When a task corresponding to a node of the plurality of graphing nodes has been completely computed, the status of the node may be set to dirty status until all asynchronous data has been loaded. Further, executing all dirty nodes of the plurality of graphing nodes in accordance with respectively assigned threading models may further comprise: re-executing a task corresponding to a node of the plurality of graphing nodes, wherein the re-execution comprises: locating one or more predecessor nodes of the node; determining whether the one or more predecessor nodes are set to dirty status; re-executing each task corresponding to the one or more predecessor nodes that are set to dirty status; and executing the task corresponding to the node of the plurality of graphing nodes.

In additional embodiments, assigning each node of the plurality of graphing nodes to one or more processing queues is accomplished by a scheduler. Also assigning each node of the plurality of graphing nodes to one or more processing queues may further comprise grouping tasks within queues by predecessor tasks or by data sources. Assigning each node of the plurality of graphing nodes to one or more processing queues may also comprise a weighted combination of: grouping tasks within queues within queues by predecessor tasks; and grouping tasks within queues within queues by data sources.

In another embodiment, a system is provided for optimizing data computed by multiple processors. The system comprises: a plurality of processors wherein: the processors are respectively coupled to a plurality of cache memories; and the processors are coupled to a common data bus; a user interface comprising a user data entry interface and a display interface; a memory for storing data and one or more instructions for execution by the plurality of processors to implement one or more functions of the data processing system to: define a plurality of tasks requiring execution; identify one or more dependencies for each respective task of the plurality of tasks, the one or more dependencies comprising at least one of a resource dependency and a memory dependency; determine dependencies between for each respective task of the plurality of tasks wherein the dependencies include directional dependencies; create a directed graph, wherein the directed graph includes: a plurality of nodes, the nodes respectively corresponding to the plurality of tasks requiring execution; and a plurality of directed edges that respectively correspond to the directional dependencies, each of said directed edges originating from a node of the plurality of nodes and terminating on another node of the plurality of nodes; and analyze the directed graph to assign execution of tasks to a plurality of processors to maximize computational efficiency. Those of skill in the relevant arts appreciate that user interfaces may include commonly used visual, tactile, and aural input and output interface elements such as keyboards, touch screens, mice or other cursor manipulation devices, displays such as LCD panels or CRT displays, printers, speakers, and microphones.

Instructions may be executed in any desired manner. In one implementation, the instructions to be executed by the plurality of processors further include instructions to attribute a threading model to each node of the plurality of nodes. Also, the instructions to be executed by the plurality of processors may further include instructions to: assign one or more threading models, where a parallel threading model to each said node where said node corresponds to a task that is independent, may operate in parallel, and has a non-blocked status; assign a strip-mine threading model to each node in a collection of nodes that correspond to tasks that operate on common data; and assign a non-threading model is assigned to nodes corresponding to tasks that must be executed sequentially.

In various embodiments, a branch prediction model may be assigned to a node of the plurality of nodes, the branch prediction model determined by an entropy characterization of data operated on by a function corresponding to the node. Further, each node of the plurality of nodes may be assigned to one or more processing queues and tasks corresponding to each node assigned to the one or more processing queues and executed. Each node of the plurality of nodes may be is assigned to one or more processing queues based on an identified memory dependency identified for that node, and the consideration of memory dependency may include a desired cache level allocation.

Node execution may also be determined by node processing status. In an embodiment, systems and methods include for each node of the plurality of nodes, determining whether the status of each node is blocked or un-blocked; and executing tasks corresponding to all non-blocked nodes of the plurality of nodes then executing tasks corresponding to all blocked nodes of the plurality of nodes. The system may further comprise repeating execution of tasks corresponding to all blocked nodes of the plurality of graphing nodes once data has become available.

An embodiment of the system of the present invention includes iterative techniques to provide continued or additional computation. The instructions to be executed by the plurality of processors may further include instructions to perform the following steps until all data is processed: setting status of all nodes of the plurality of nodes to processed or unprocessed status; when a task corresponding to a node of the plurality of nodes has been completely computed, setting status of the node to processed status; when data corresponding to a node of the plurality of nodes has been changed, setting status of the node to unprocessed status; and executing tasks corresponding to all unprocessed nodes of the plurality of nodes in accordance with respectively assigned threading models.

An embodiment also provides a fluorescence compensation system that comprises: a plurality of detectors coupled to a communication bus; a plurality of processors, each respectively coupled to a cache memory and the communication bus; a memory coupled to the communication bus, the memory containing instructions to be executed by the one or more processors to: load a data file, the data file comprising dye response data from the plurality of detectors for one or more dyes; analyze spectral response from each detector for the plurality of detectors; identify which of said plurality of detectors detected a dye from the one or more dyes within a predetermined detection threshold; and calculate a spectral overlap for each dye of the one or more dyes to compute a fluorescence compensation matrix. The instructions may be executed by the one or more processors to store the compensation matrix in the memory for analysis with the dye response data.

BRIEF DESCRIPTION OF THE DRAWINGS

The features, objects, and advantages of embodiments of the disclosure will become more apparent from the detailed description set forth below when taken in conjunction with the drawings, in which like elements bear like reference numerals.

DESCRIPTION OF VARIOUS EMBODIMENTS

Reference will now be made in detail to the present exemplary embodiments of the invention, examples of which are illustrated in the accompanying drawings.

Figure 1:
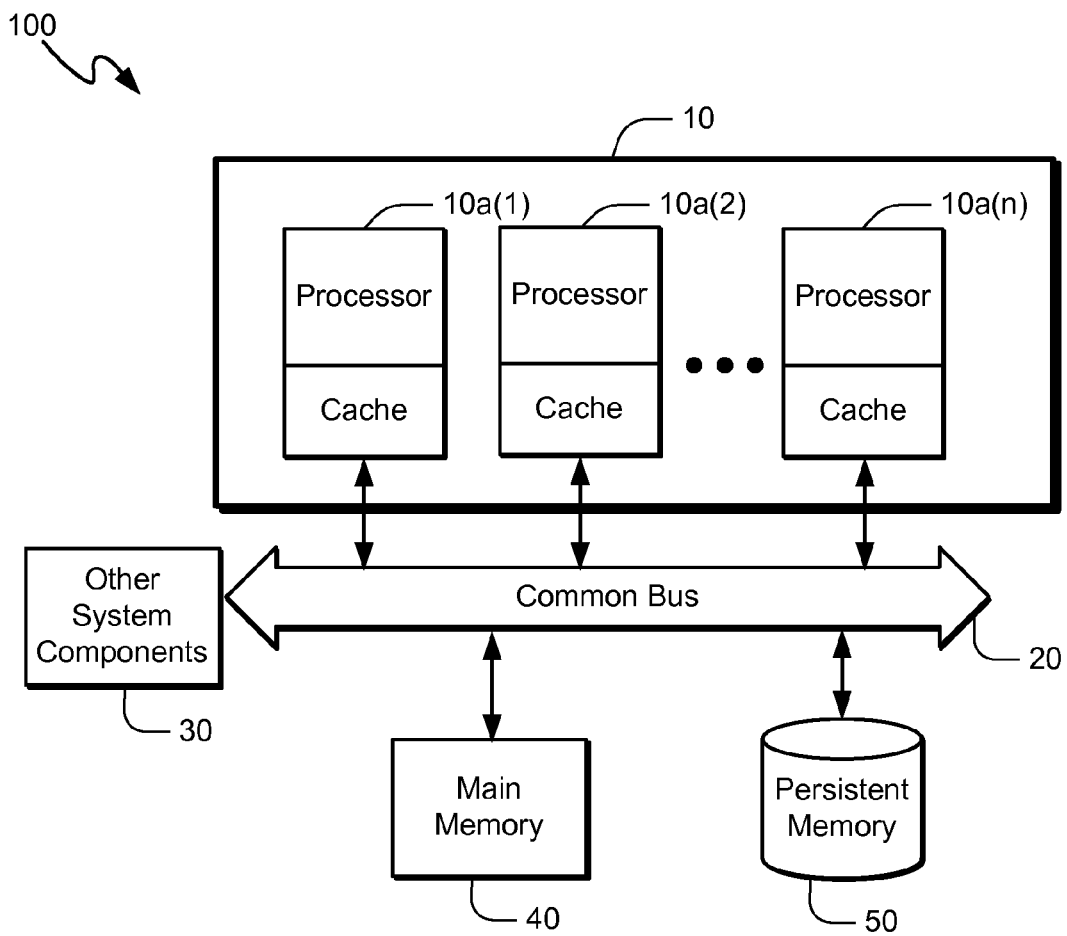
FIG. 1 is an illustration of an exemplary embodiment of a multiprocessor system of the present invention.

An embodiment of the hardware components of the present invention are illustrated in FIG. 1. The system 100 includes a pool 10 of processors 10a(1), 10a(2) through 10a(n), where n may comprise any number of processors. The processors 10a(n) from the processor pool 10 are respectively coupled to a common bus 20, which relays data to and from other system components 30 such as displays, keyboards, mice, peripherals, sensors, detectors, storage devices, and the like; main memory 40 such as volatile dynamic random access memory (DRAM); and persistent memory 50 such as a hard drive, FLASH memory, CDRWs DVD+/−RWs and the like. Those of skill in the relevant arts appreciate that the system 100 may comprise a unitary or federated computer system, a personal computer system, a networked system of computing components, or distributed computers interconnected through a network such as the Internet via protocols such as TCP/IP. The bus 20 may comprise a local computer bus, a plurality of local computer busses, a network connection bus and protocol such as Ethernet, or any combination thereof.

Each processor 10a further comprises a processor element and a cache element for storing frequently-accessed information. In general, caches are utilized in computer systems to increase performance by decreasing the access time required to write or retrieve data from main memory. Caches generally comprise memory with decreased access time and/or latency, and memory locations within the cache store copies of the data from the most frequently used main memory locations. As long as most memory accesses are to cached memory locations, the average latency of memory accesses will be closer to the cache latency than to the latency of main memory.

In one implementation, each processor 10a comprises a core of a microprocessor such as a Pentium dual core or quad core processor, an AMD multi-core processor, a core of a CELL processor, or the like. In certain implementations such as those shown in FIG. 1, each processor core includes dedicated cache memory to increase performance by decreasing data storage and retrieval latency as opposed to more lengthy times required to access main memory. In certain implementations, the plurality of caches operate independently of each other, but in alternate embodiments, each of the caches in the processor pool operate coherently, that is, for example, data values that are duplicated among caches are maintained at the same value based on independent computation from each of the processors 10a. Those of skill in the art also understand that a multilevel cache scheme may also be employed to better utilize the resources of the system 100.

In one embodiment of the present invention, users utilize the system 100 to create plots in order to explore their data and produce results. These plots are a combination of one or more parameters within the data. Traditionally users will create a plot and select the parameters that the plot is graphing. For creating a large number of plots this is a tedious process and the user does not see the data until the plots are created. In one embodiment, all combinations of parameters of the data are automatically produced as plot thumbnails and the user creates plots by selecting the thumbnails in the user interface (e.g. by clicking). Thus, the user can select and create plots by looking at the data, rather than having to create the plot then look at the data. The thumbnails update based upon the users' focus within the application; if the user had selected an analysis region then the thumbnails may update based on that analysis region; if the user had selected a gate then the thumbnails may update based on that gate. The user can select subsets of plot thumbnails to add in a single operation.

The user may wish to filter the parameters that are displayed as thumbnails and a user interface may allow selection of this, or a heuristic may filter the parameters (e.g. parameters not used in the current gate), or the user may select a profile for a particular type of input data based on matching keywords and values within the input data, or associated metadata.

The thumbnails may only initially display a partial set of the data, in many cases where the data is distributed randomly this may be sufficient to allow the user to begin working whilst the whole set of data is calculated in the background. Once the whole set of data is calculated, the thumbnails update. The partial subset may be user selectable or the application may choose; options may be a fixed number of events from the start of the data, a random sampling of the data, or a semi random sampling based on the user's selected context within the user interface (e.g. if the user was looking at a gated subset of data, then using elements from that subset plus elements from the whole data set may give a realistic representation of the whole data set).

In various embodiments of the present invention, users perform an analysis using the tools within the application to transform the data, to find subsets of data, and to produce statistical and graphical output.

Figure 2:
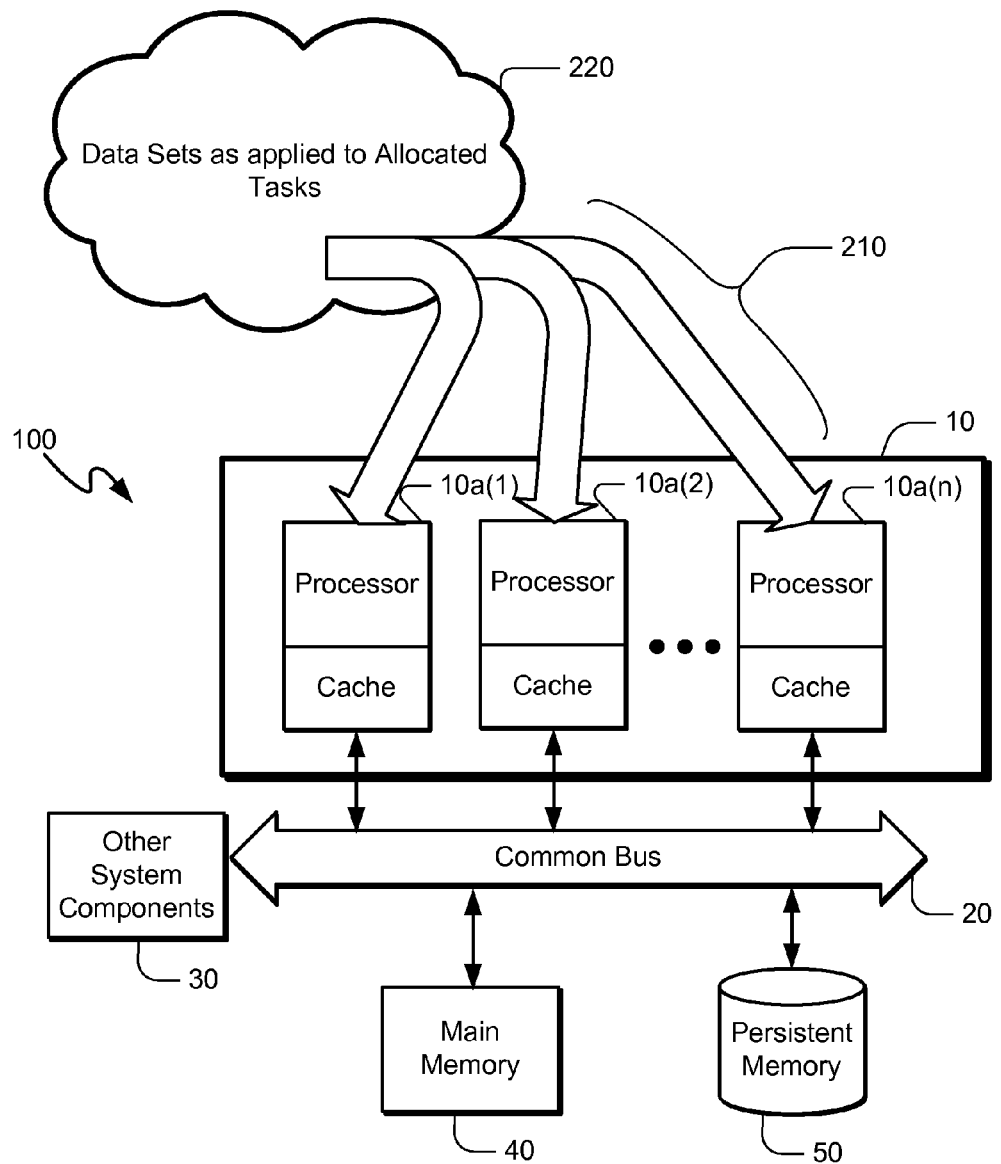
FIG. 2 is an illustration of an exemplary embodiment of a multiprocessor system of the present invention showing task allocation by processor.
Figure 2A:
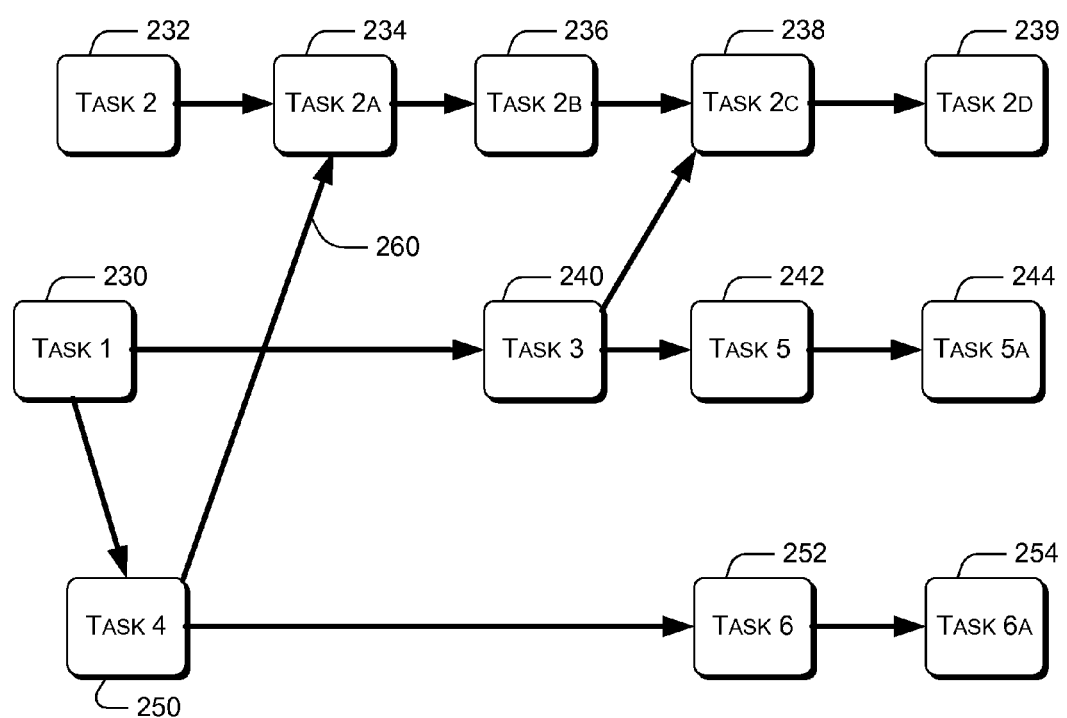
FIG. 2A is a representation of a directed graph utilized by embodiments of the present invention.

In one embodiment, the application maps the user designed analysis into a mathematical construct called a directed graph (See, e.g., FIG. 2A). Those of skill in the art appreciate that a directed graph represents a set whose elements are called vertices or nodes, and includes a set of ordered pairs of directed edges connecting the vertices or nodes. In various embodiments of the present invention, operations or data represent the vertices or nodes in the graph construct (see FIG. 2A, 230, 232, 234, 238, 238, 239, 240, 242, 244, 250, 252, 254), and the dependencies between are tasks represented by directed edges (see FIG. 2A, arrows such as 260). The directional dependency relationships reflect the temporal relationships of tasks; that is, some tasks cannot be completed before a predecessor task is complete (e.g. a density plot task requires a dual parameter histogram task to be complete). Put another way, when it is desired to analyze data to produce a result, the analysis is decomposed into a set of operations that can be performed on that data. Some of the operations become predicated on the results of other operations and so there is a dependency between the operations; that is, some operations cannot be computed until the other operations have completed. By representing the analysis as a directed graph, graph algorithms can then be used to identify the order in which the tasks should be processed. Further, embodiments of the present invention may utilize the directed graph to determine a minimum number of nodes that need to be processed to achieve a particular result, thereby minimizing the computation time and expense.

Figure 2B:
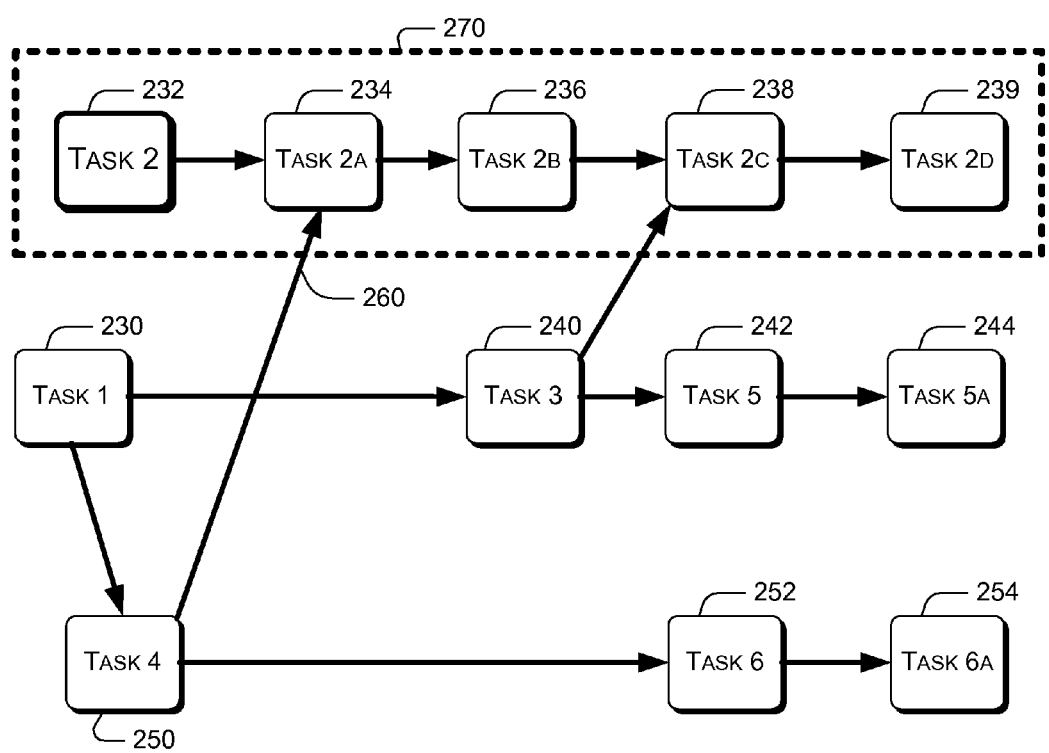
FIG. 2B is a representation of a directed graph utilized by embodiments of the present invention where nodes have been marked with a "dirty" status.

A filtered view of the task graph is produced using a subset of the tasks; that is, the tasks that are 'dirty' and their dependents. A task is 'dirty' if it has not been calculated yet or its state or data has changed so that it requires recalculation. A dependent task of a dirty task will also need recalculation as it is using products of the dirty task. In one implementation, a visitor algorithm is applied to the graph to mark a dirty node and all its children as dirty. In this embodiment, the graph may be filtered so that only dirty nodes remain, and only the dirty nodes need be recalculated to obtain the desired result. For an example, refer to FIG. 2B, where Task 2 (232) has become "dirty" because, for instance, its data became out of date. Then all of its dependent "children" tasks (Tasks 2A-2D) will need recalculation. In FIG. 2B, as only the tasks within the dashed area 270 require recalculation when Task 2 (232) becomes "dirty," computational effort and cost is saved as the remaining nodes do not require re-computation.

Figure 2C:
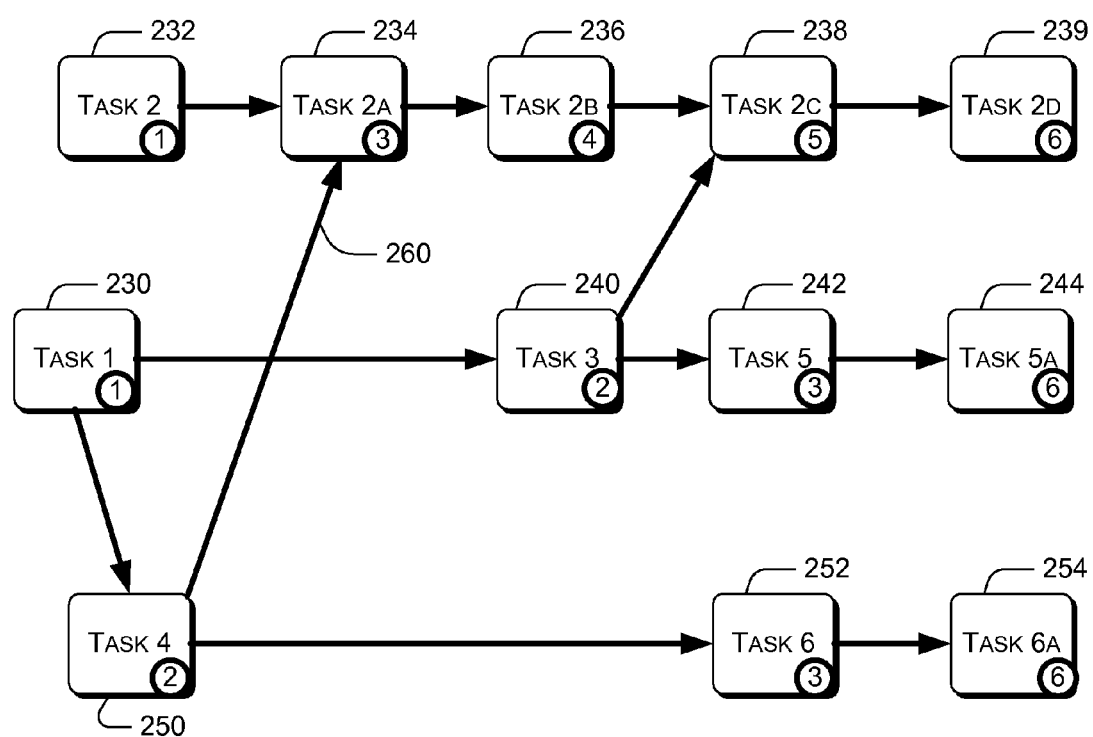
FIG. 2C is a representation of a directed graph utilized by embodiments of the present invention where nodes have been marked with a generation number indicia.

The order of evaluation of tasks is then calculated using Dijkstra's Shortest Paths algorithm applied to the graph. Each task is assigned to a generation, with each generation ordinally numbered. Referring to FIG. 2C for example, Tasks 1 and 2 (230, 232, respectively) are assigned to generation 1 (see small circled number within each task). Subsequent tasks are assigned to generations (Tasks 3 and 4 to generation 2, Tasks 2A, 5, and 6 to generation 3, Task 2B to generation 4, Task 2C to generation 5, and Tasks 2D, 5A, and 6A to generation 6). Each task within a generation does not depend on any other task within the same generation, and therefore these tasks may be executed in parallel by a multitude of processing units, further improving execution speed and efficiency.

Figure 2D:
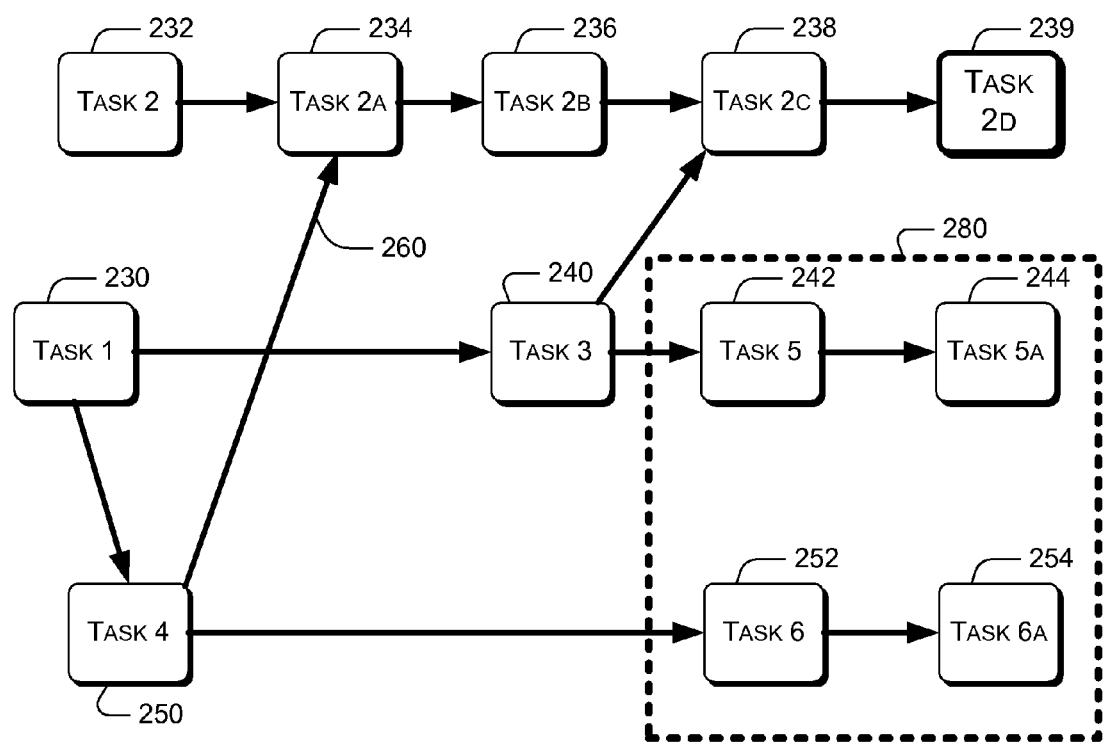
FIG. 2D is a representation of a directed graph utilized by embodiments of the present invention where nodes have been identified as not needing processing because of independence from predecessor nodes.

An additional refinement includes the ability to calculate a partial set of the task graph that includes the predecessors of a specified task. This provides functionality such as the ability to interactively manipulate a subset of the user analysis in response to user interaction and just perform the calculations needed for that action rather than calculating all products that may be affected by the action. Another example includes the situation where a user is interested in a limited portion of the analysis such as the statistical results, where just the involved tasks are calculated rather than all the other products within the analysis. For an example, by analyzing the predecessors for a given node (see FIG. 2D, Task 2D (239)), we can calculate the minimum set of nodes required to obtain the desired result. The nodes within the dashed box 280 do not need calculating, as they do not affect Task 2D (239). This approach may be combined with the dirty node functionality mentioned above to further reduce the set of nodes.

Some tasks are dependent on the number of elements within the input data set (generally they perform an operation on each element within the set) while other tasks are independent of the number of elements within the input data set (e.g. they take constant time, for example, producing a density plot bitmap from a dual histogram plot is dependent on the dimensions of the density plot and not the input data set). Some of these tasks therefore require all elements within the input data set to be present in order to execute, whereas some tasks can execute on a subset of the input data, and then when the rest of the input data is available, execute on the rest of the input data. But other tasks that require the whole input data to be available cannot execute, or if they are executed, will need to re-execute when the whole set is available, which adds to overall execution time.

Because of this, in an embodiment, tasks are classified into blocking and non-blocking tasks. A blocking task is a task that requires the entire data set to be present to execute. A non-blocking task, on the other hand, can be performed on incremental sets of data. Examples of blocking tasks include calculating statistics from histograms, producing density plot bitmaps from dual parameter histograms, and analysis regions that adjust based on the profile of the input data. Examples of non-blocking tasks include performing fluorescence compensation, calculating computed parameters, and building histograms.

Figure 2E:
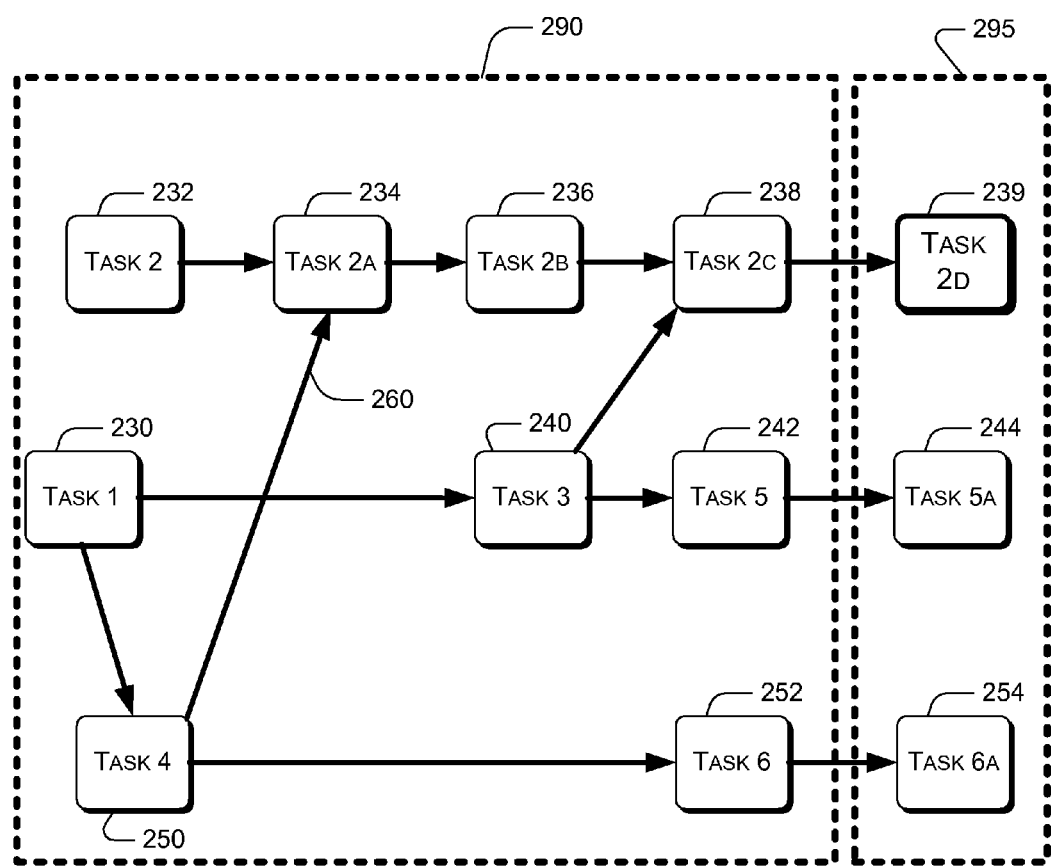
FIG. 2E is a representation of a directed graph utilized by embodiments of the present invention where nodes have been partitioned into blocking and non-blocking nodes.

Since a non-blocking task may depend on a blocking task (e.g. producing a histogram based on a region that adjusts according to the input data), it cannot be executed until the blocking task has completed, and therefore the task graph is partitioned into blocking and non-blocking sub graphs. The non-blocking sub graph can be executed with incremental amounts of data, whereas the blocking sub graph requires all data to be present (or the application can elect to re-compute the whole blocking sub graph tasks multiple times, for example to provide updates to the user while waiting on an external event, such as hard disc access, or data from an instrument). FIG. 2E illustrates an exemplary partition of a directed graph into blocking nodes 295 and non-blocking nodes 290. The partition is established so that any descendants of blocking nodes are in the blocking partition even if the descendant is non-blocking.

In cases where all the input data set may not be immediately available, progress can be made while waiting for the input data. For example, when loading a file from a disk, the disk may provide data at a slower rate than it is possible to perform all the tasks on it, so the application performs non-blocking calculations on blocks of data as they arrive from the disk, and once all data has arrived from the disk, the blocking calculations can execute. If the application finds itself still waiting for data from the disk even after non-blocking calculations have executed, it may elect to perform the blocking calculations so as to provide feedback to the user, even though it would have to perform those blocking calculations again once the whole input data set is available. Since it was waiting on the external event of data arriving from the disk anyway, this may not affect the total elapsed time from starting disk loading to the final results being available to the user.

In an embodiment of the present invention, within each build generation of tasks, tasks are grouped as to a threading preference. In one implementation, there are three threading preferences available: DoNotThread, Parallel, and Stripmine. This enables further optimization of performance for a number of reasons.

Modern microprocessors are much faster than the memory that they are connected to, and therefore accessing memory is slow and involves the processor waiting on memory to deliver data or instructions to it. Microprocessors compensate for this by having a set of local very fast memory cache. When data is requested, it is fetched into this cache, and the subsequent access to memory that is in already in the cache is much faster. The amount of cache is small compared to the main memory size however, and infrequently used data is evicted from the cache to main memory.

Because the cache size is limited, if a set of data can be worked on within the cache repeatedly, performance of the system is greatly increased as the processor does not have to wait on the cache. Thus, if tasks can be grouped by those tasks that use the same set of data on the same processor, there is an increased likelihood that as each task executes, the data for the task will be within the processor's cache and therefore performance is increased. Turning to FIG. 2, in a system 100 that has multiple processors 10*a*(1) through 10*a*(n), where n may represent any number of processors, (or alternatively, processor cores) whole data sets 220 can be partitioned 210 into subsets that fit within a cache, and each processor 10*a* in the pool of processors 10 takes an individual partition and executes the tasks on the data in the partition. Once a processor has completed a partition, it is allocated the next available partition that has not been executed. In the present invention, this task-cache allocation process may be referred to as "stripmining." As some partitions may execute faster than others (due to properties of the input data, such as a temporal element to the user's experiment), this helps to balance out the processing load across processors 10*a* as they are less affected by any variation in the execution time of partitions of the input data set.

Clearly only some tasks are suitable for this mode of execution; some tasks require access to the same set of output data and therefore would require a locking mechanism to synchronize access to the output data amongst multiple processors. Synchronizing access to data slows the processors as they may need to wait for a lock to be available. In some types of tasks it may be possible for each processor to work on a private set of output data and in a final combining step once all processors have finished collate the private output data; this would typically be a constant time operation or dependent on number of processors. The decision on whether to execute a task in this manner may therefore be dependent on the size of the input data relative to the collation time; for small amounts of input data the collation time may be greater than the time to execute the private data. A task could estimate the execution time given the input data, or use a measurement of execution time from a previous run to allow the system to decide whether to execute the task in a stripmine fashion.

Another advantage of stripmining is that where the output data of a task has a 1 to 1 correspondence with the input data but the output data is shared between tasks (e.g. the task is writing a single bit per element of the input data into a word of memory per element), there is no need for locking within the task, and the task executes in a lock free manner.

It may be advantageous to sort the stripmining tasks within a build generation by their links to input data; this has the advantage on a processor with multiple levels of cache that consecutive tasks have a greater chance of finding their data within nearer (and thus, faster) levels of cache within the processor.

Parallel tasks are tasks where it is better to assign tasks to a pool, and each processor within the system is assigned a task from the pool. The processor executes the task, and upon completion is assigned another task from the pool until the pool is empty. These tasks may be examples such as building a two dimensional histogram, where the access pattern of writes and reads to the histogram is relatively random because it is dependent on random unpredictable input data, and this histogram is large relative to the cache size and therefore it is advantageous to keep the histogram in the cache rather than the input data.

Some tasks may not be safe to execute in parallel, and therefore require execution in sequence. Embodiments refer to these tasks as DoNotThread tasks, and they are executed sequentially by the system.

In a non-limiting exemplary embodiment, data within the application is stored within a Structure of Arrays format. The file formats that certain embodiments consume often present data as an Array of Structures format. The Array of Structures format lays out data as the parameters for each event being contiguous, repeating for each new event. If there were 6 parameters per event, then the first 6 locations of memory would represent the 6 parameters of the first event, the next 6 locations would represent the 6 parameters of the second event, and so on. In contrast, the Structure of Arrays format groups by parameter rather than event, so that the first 6 locations in memory would be the value of the 1st parameter for the first 6 events.

As most of the tasks only require the use of one or two parameters, this drastically reduces the amount of memory that must be accessed to execute the task, as memory is brought into the processor in cache line sizes, which may be 64 bytes or more. Instead of requiring access to (total number of parameters)×(number of events) memory locations, embodiments may only need to access (number of parameters required by task)×(number of events) memory locations during execution of the task.

The Structure of Arrays (SoA) format also provides greater opportunity for using vector instructions on the processor. These instructions can perform multiple operations simultaneously on elements within contiguous memory. As the same operation is often performed on the elements of a parameter, this increases performance. For the AoS format, this may not be possible as the elements of the same parameter are not contiguous within memory.

Modern microprocessors may contain logic to predict which way a branch in program execution will be taken, and perform speculative work beyond the branch ahead of time. When the logic mispredicts the branch there is a significant penalty as the processor has to throw away the speculative work and restore its internal state. When it predicts correctly, performance is improved however.

Often the operations within a system depend on input data that has a large degree of randomness. Where the input data is random the branch prediction does not perform well. For some algorithms it may be possible to implement them as variations that use a branch or do not use a branch. If the amount of randomness within the input data can be measured, it is possible to select a branched implementation for less random data, and a branchless implementation for random data. Depending on the relative execution time of the implementations, the level of randomness can be chosen as to where to switch between the implementations.

The measurement of the level of randomness may be derived from a predecessor task's results. For example, a count of events within a gate relative to the total event count will give an indication of the randomness of the gated data for gating. Alternatively it may in some cases be actually faster to measure the randomness of the data and then use either implementation of the algorithm.

In some data sets, the randomness over the whole data set may vary, e.g. where a user has added a reagent mid experiment that then affects the subsequent data, and hence it's randomness. For example, 50% of the data may fall within a gate, but because the gate was on a kinetics experiment, the 50% occurs at the first 50% of the data set. This would ordinarily imply selection of a branchedless implementation, which would actually reduce performance. By measuring the randomness of subsets of the data, different implementations can be applied to the algorithm to different subsets, and this would solve the performance issue, and for sufficiently large subsets the cost of the sub-measurement can be amortized.

Since analysis tools (e.g., gates, regions, plots) essentially work with any numerical data, the same set of tools can be used to analyze results from entire sets of data. For example, but not by way of limitation, a protocol for a users' experiment may produce a series of statistics (for example CD4 count, CD8 count). But if the user has a whole series of data files analyzed using the same protocol, then these statistics form a multi-parameter dataset themselves, which can in turn be analyzed using the same toolset. Instead of each 'event' represents a cell or other particle, each event represents a whole sample that the user has analyzed. Thus, a researcher could use the same tools he uses for analyzing a single file to analyze a whole study, and look for populations of samples within the study.

Figure 3:
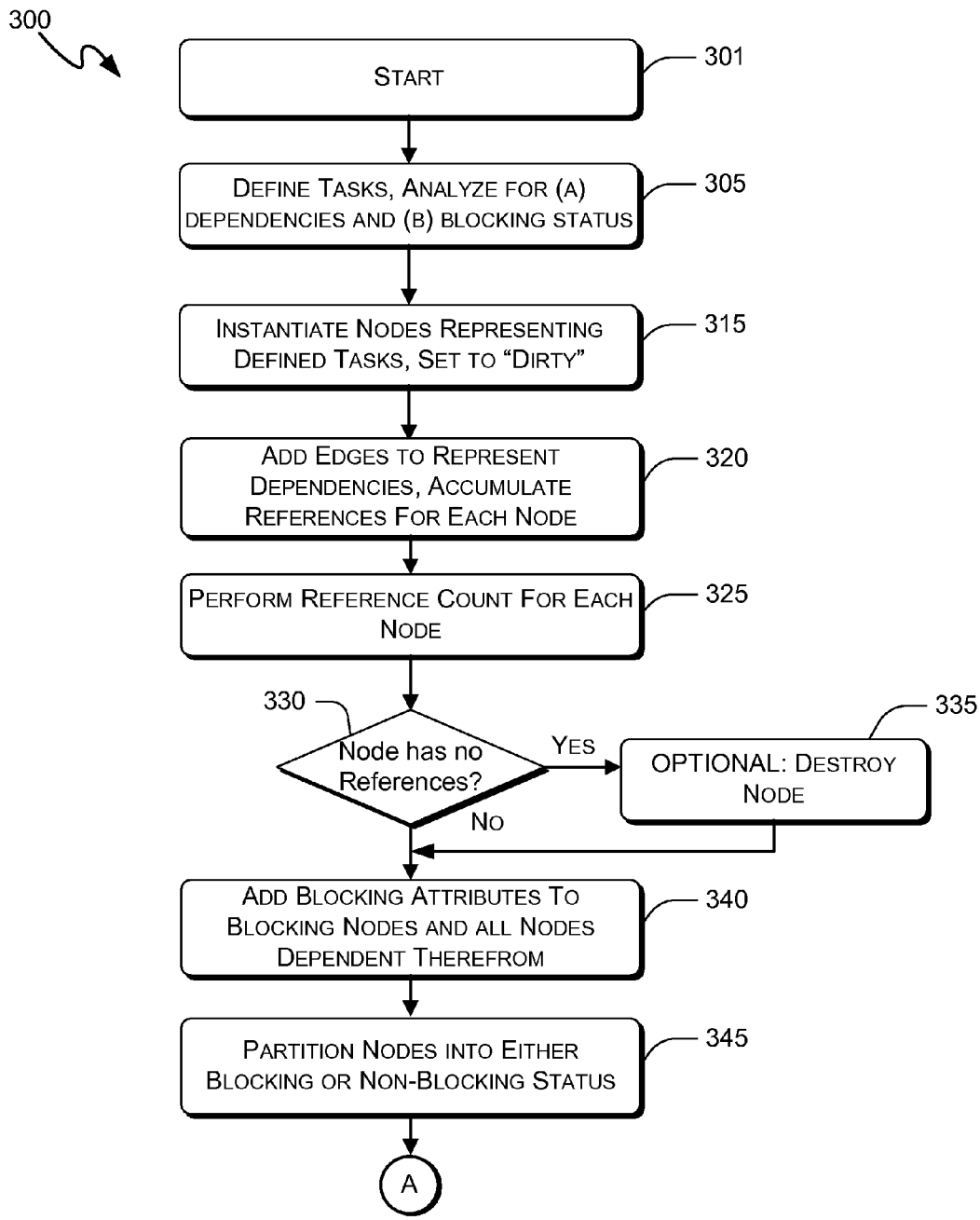
FIG. 3 is an illustration of an exemplary embodiment of a flowchart depicting a method of the present invention.
Figure 4:
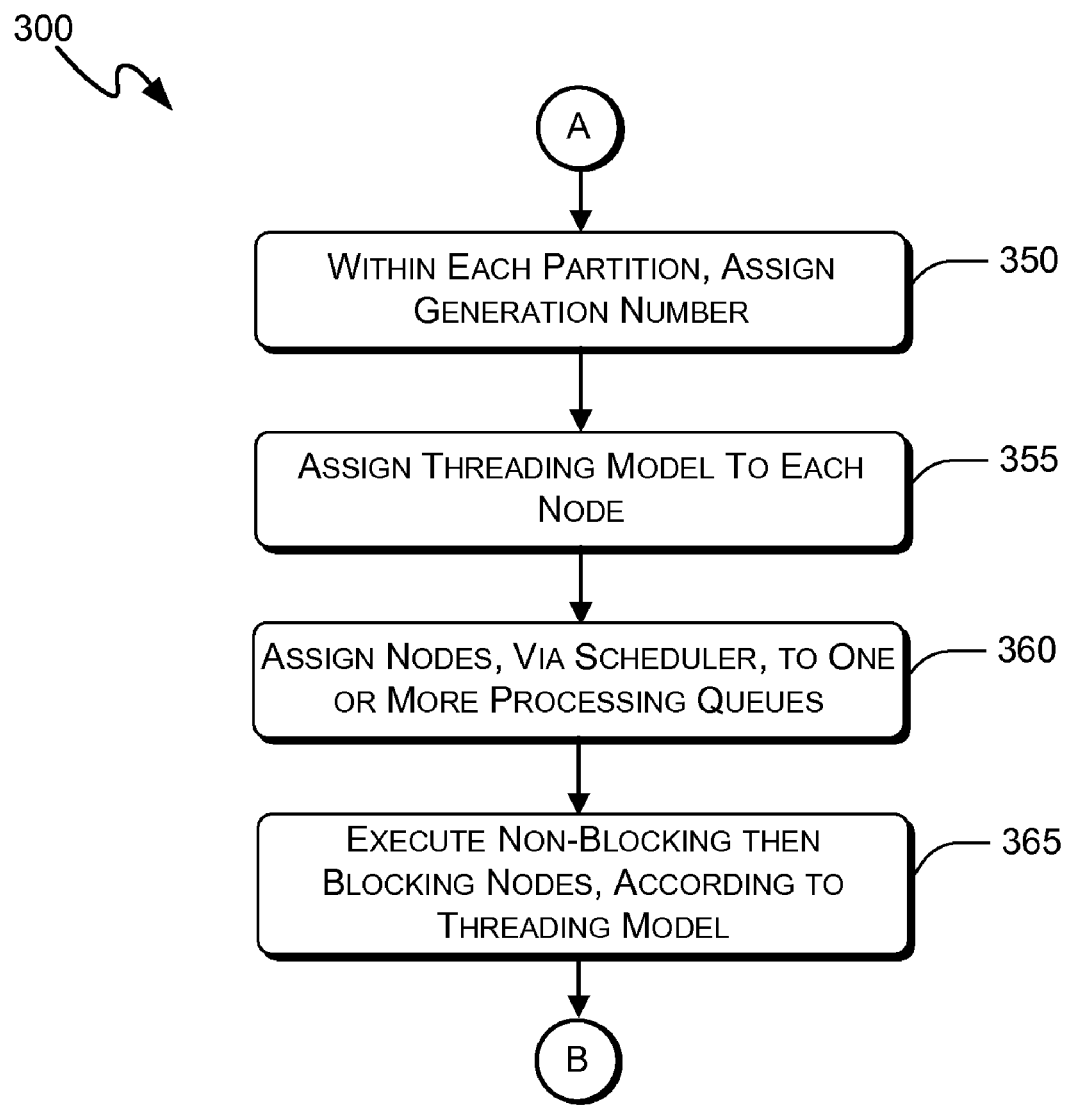
FIG. 4 is a continued illustration of an exemplary embodiment of a flowchart depicting a method of the present invention.
Figure 5:
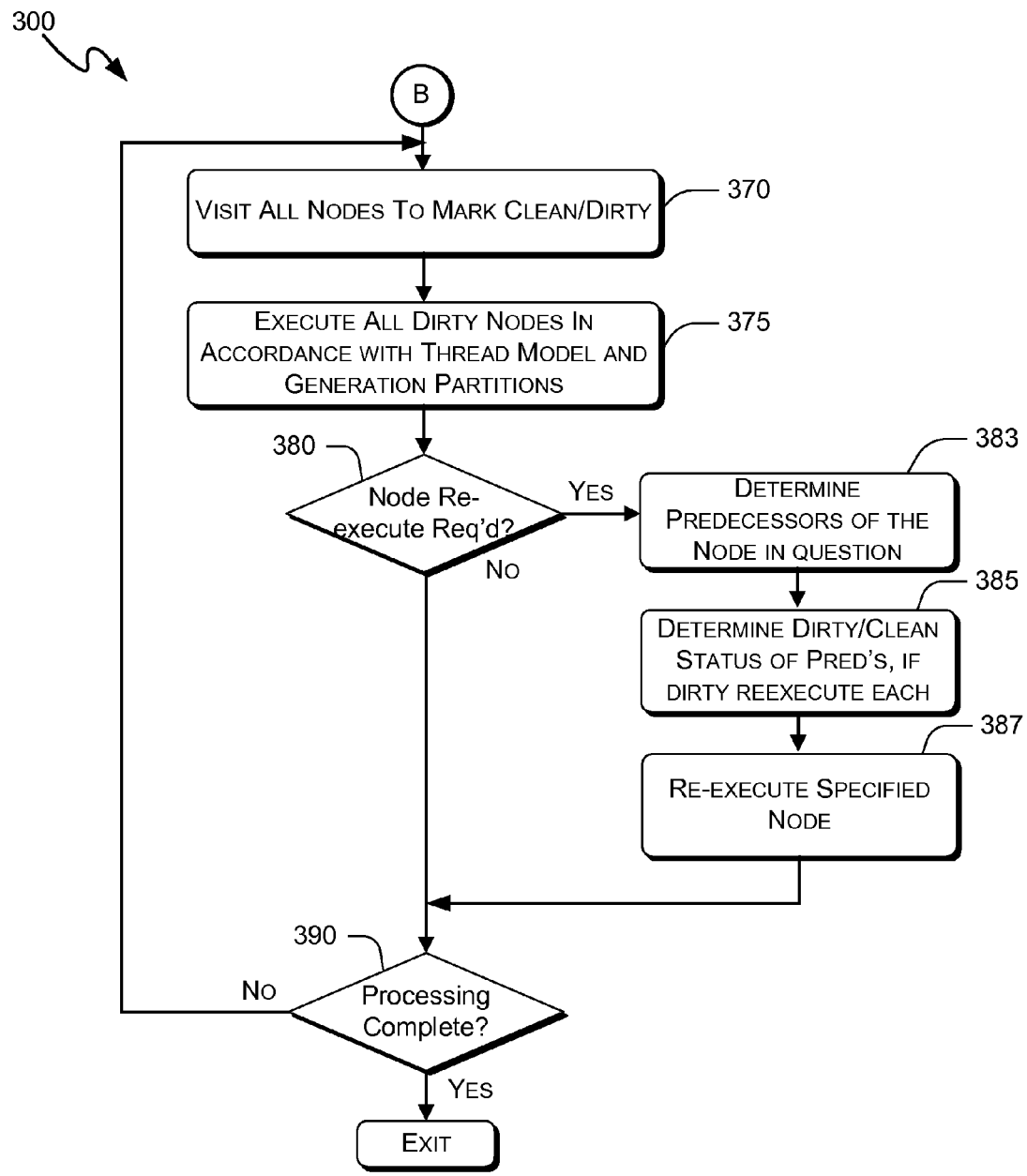
FIG. 5 is a continued illustration of an exemplary embodiment of a flowchart depicting a method of the present invention.

Embodiments of the present invention may be better understood when considering the flow chart 300 shown in FIGS. 3-5. Initially, tasks necessary to complete the particular analysis are defined. The tasks are analyzed for dependencies and are analyzed for blocking/non-blocking status 305. Nodes may then be instantiated to represent the defined tasks whereupon an indicia associated with node data structures are initially set to "dirty" 315. Edges may then be added to represent the dependencies between nodes 320, for example, references are added when a node has an edge directed to it, and a reference is not added when a node has an edge originating from it.

For each node, a reference count is performed 325. If after assigning all nodes and edges, a node has no references, then nodes may be optionally deleted 330, 335. Blocking attributes are added to blocking nodes and all nodes in all generations dependent therefrom 340, and the set of nodes is partitioned by blocking/nonblocking status 345. Within each partition, data structures associated with the nodes are assigned 350 a generation number. For example, generation 1 is assigned to nodes with no dependencies, and generation 2 is assigned to nodes dependent upon generation 1. Nodes that depend from a generation "n−1," where n is any arbitrary generation number, are assigned generation number n. If a node has multiple dependencies, then generation of the node is set to be the maximum of the node's parent node generations plus 1.

Threading models are assigned 355 to each node, including an optional branch prediction 355. In one embodiment, a threading model may be assigned as (a) a parallel model, when nodes are independent and non-blocking; (b) a Stripmine model, when nodes operate on common data; (c) a Do Not Thread model for tasks that must be executed sequentially; and (d) combinations of those factors that may be desirable for conditions such as load balancing.

Nodes may be assigned to one or more processing queues by any method, such as via a scheduler 360. If task is designated with a Strip-mine threading model, each data range is iteratively computed for each task. In one embodiment, assignment to processing queues may be performed by (a) grouping tasks within queues by predecessor tasks, (b) grouping tasks within queues by data sources, or a weighted combination of (a) and (b).

Execution of nodes may be undertaken in any desired manner. For instance, non-blocking nodes may be executed first, then blocking nodes according to threading model 365. Non-blocking node execution may occur multiple times before blocking node computation, if desired. Examples include data that has partially been loaded. Blocking node execution may be repeated for interim calculations or after all data becomes available.

Iteration may then be undertaken to perform a full, partial, or incremental analysis. As part of the iteration process, all nodes are visited 370 to mark their processing status as "clean" or "dirty" (i.e. processed, or unprocessed). Once all nodes are computed, then they are marked as clean, meaning their computation is completed. If data is being loaded asynchronously, nodes are assigned dirty status until the last pass is complete. If a node's data has changed since previous calculation, the node and the node's dependent nodes are assigned dirty status.

All dirty nodes are executed 375 in accordance with previous thread model/generation partitions. To re-execute 380 a task corresponding to a node somewhere in the graph, its predecessors are determined 383, and it is determined 385 whether the node and/or its ancestor nodes are dirty 385. If a node is dirty, each relevant predecessor task is re-executed 385, and then the task corresponding to the specified node is executed 387. This process continues 390 until data is entirely processed (for instance, no more screen updates remain).

It is to be understood that the foregoing description is exemplary and explanatory only and is not restrictive of the invention, as disclosed or claimed.

The accompanying drawings, which are incorporated in and constitute a part of this specification, illustrate several embodiments of the invention and together with the description, serve to explain the principles of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for processing data comprising:
    defining a plurality of tasks requiring execution;
    identifying one or more dependencies for each respective task of the plurality of tasks, the one or more dependencies comprising at least one of a resource dependency and a memory dependency;
    determining dependencies between for each respective task of the plurality of tasks wherein the dependencies include directional dependencies;
    creating a directed graph, wherein the directed graph includes:
        a plurality of nodes, the nodes respectively corresponding to the plurality of tasks requiring execution; and
        a plurality of directed edges that respectively correspond to the directional dependencies, each of said directed edges originating from a node of the plurality of nodes and terminating on another node of the plurality of nodes; and
    analyzing the directed graph to assign execution of tasks to a plurality of processors to maximize computational efficiency;
    performing the following steps until all data is processed:
        setting status of all nodes of the plurality of nodes to processed or unprocessed status;
        when a task corresponding to a node of the plurality of nodes has been completely computed, setting status of the node to processed status;
        when data corresponding to a node of the plurality of nodes has been changed, setting status of the node to unprocessed status; and
        executing tasks corresponding to all unprocessed nodes of the plurality of nodes in accordance with respectively assigned threading models.

2. The method as defined in claim 1, further comprising attributing a threading model to each node of the plurality of nodes.

3. The method as defined in claim 2 wherein attributing a threading model to each node of the plurality of graphing further comprises:
    assigning a parallel threading model to each said node where said node corresponds to a task that is independent, may operate in parallel, and has a non-blocked status;
    assigning a strip-mine threading model to each node in a collection of nodes that correspond to tasks that operate on common data; and
    assigning a non-threading model is assigned to nodes corresponding to tasks that must be executed sequentially.

4. The method as defined in claim 3 wherein for each node assigned with a strip-mine threading model, iteratively computing each corresponding task for each data range associated with the task.

5. The method as defined in claim 3 wherein a strip-mine threading model comprises:
    partitioning a data set into a plurality of subsets, the size of each subset of the plurality of subsets chosen to be containable within a cache memory of predetermined size associated with a processor of the plurality of processors;
    allocating processing of a subset of the plurality of subsets to the processor;
    loading the subset of the plurality of subsets into the cache memory associated with the processor;
    executing a task utilizing the subset of the plurality of subsets; and
    indicating, by the processor, that another subset of the plurality of subsets may be allocated.

6. The method as defined in claim 3 wherein multiple threading models may be assigned to any node of said plurality of nodes.

7. The method as defined in claim 1 wherein a branch prediction model is assigned to a node of the plurality of nodes, the branch prediction model determined by an entropy characterization of data operated on by a function corresponding to the node.

8. The method as defined in claim 1, further comprising assigning each node of the plurality of nodes to one or more processing queues and executing tasks corresponding to each node assigned to the one or more processing queues.

9. The method as defined in claim 8, wherein each node of the plurality of nodes is assigned to one or more processing queues based on the an identified memory dependency identified for that node.

10. The method as defined in claim 9, wherein the memory dependency includes a desired cache level allocation.

11. The method as defined in claim 8 wherein executing tasks assigned to the one or more processing queues further comprises:
    for each node of the plurality of nodes, determining whether the status of each node is blocked or un-blocked; and
    executing tasks corresponding to all non-blocked nodes of the plurality of nodes then executing tasks corresponding to all blocked nodes of the plurality of nodes.

12. The method as defined in claim 11 wherein executing tasks corresponding to all blocked nodes of the plurality of nodes further comprises repeating execution of tasks corresponding to all blocked nodes of the plurality of graphing nodes once data has become available.

13. A method for optimizing utilization of processor resources comprising:
    determining a plurality of processing tasks required to perform a requested computation and obtaining from the plurality of processing tasks a set of task dependencies;
    determining, from the plurality of processing tasks and task dependencies, a blocking state for each of the plurality of processing tasks and setting the blocking state to blocked or non-blocked;
    instantiating a plurality of graphing nodes respectively representing the plurality of processing tasks wherein said plurality of nodes are initialized to a dirty state;
    defining a set of directed edges between pairs of individual nodes from the plurality of graphing nodes;
    counting references for each node of the plurality of graphing nodes;
    adding blocking attributes to one or more nodes of the plurality of graphing nodes;
    partitioning the plurality of graphing nodes into a blocked set and an non-blocked set;
    within each of the blocked set partition and the non-blocked set partition, assigning a generation number to each node of the plurality of graphing nodes;
    attributing a threading model to each node of the plurality of graphing nodes;
    assigning each node of the plurality of graphing nodes to one or more processing queues;
    executing tasks assigned to the one or more processing queues;
    performing the following steps until all data is processed:
        setting status of all nodes of the plurality of graphing nodes to clean or dirty status;
        when a task corresponding to a node of the plurality of graphing nodes has been completely computed, setting status of the node to clean status;
        when a data corresponding to a node of the plurality of graphing nodes has been changed, setting status of the node to dirty status; and
        executing all dirty nodes of the plurality of graphing nodes in accordance with respectively assigned threading models.

14. The method as defined in claim 13 wherein defining a set of directed edges between pairs of individual nodes from the plurality of graphing nodes further comprises:
    adding a node reference to a node from the pair of individual nodes when the node has at least one of the set of directed edges directed to it; and
    not adding a node reference to a node from the pair of individual nodes when the node has at least one of the set of directed edges originating from the node.

15. The method as defined in claim 13 wherein counting references for each node of the plurality of graphing nodes further comprises removing a node of the plurality of graphing nodes if the node has zero counted references.

16. The method as defined in claim 13 wherein assigning a generation number to each node of the plurality of graphing nodes further comprises:
    assigning a node a generation number of 1 if the node has no directed edges terminating at the node;
    assigning a node a generation number of n if the node has a single directed edge terminating at the node that originated from a generation n−1 node;
    if the node has multiple directed edges terminating at the node, assigning the node a generation number equal to 1 plus the maximum number of the generation number of the nodes from which the multiple directed edges originate.

17. The method as defined in claim 13 wherein adding blocking attributes to one or more nodes of the plurality of graphing nodes further comprises:
    for each node of the plurality of graphing nodes, adding a blocking attribute to the node if:
        the node corresponds to a task with a blocked blocking state; or
        the node has a directed edge terminating at the node and the originating node of the directed edge has a blocked blocking state.

18. The method as defined in claim 13 wherein attributing a threading model to each node of the plurality of graphing nodes further comprises:
    assigning a parallel threading model to each said node where said node corresponds to a task that is independent, may operate in parallel, and has a non-blocked status;
    assigning a strip-mine threading model to each node in a collection of nodes that correspond to tasks that operate on common data; and
    assigning a non-threading model is assigned to nodes corresponding to tasks that must be executed sequentially.

19. The method as defined in claim 18 wherein multiple threading models may be assigned to any node of said plurality of graphing nodes.

20. The method as defined in claim 18 wherein a branch prediction model is assigned to a node, the branch prediction model determined by an entropy characterization of data operated on by a function corresponding to the node.

21. The method as defined in claim 18 wherein for each node assigned with a strip-mine threading model, iteratively computing each corresponding task for each data range associated with the task.

22. The method as defined in claim 13 wherein executing tasks assigned to the one or more processing queues further comprises executing tasks corresponding to all non-blocked nodes of the plurality of graphing nodes then executing tasks corresponding to all blocked nodes of the plurality of graphing nodes.

23. The method as defined in claim 22 wherein executing tasks corresponding to all non-blocked nodes of the plurality of graphing nodes further comprises repeating execution of tasks corresponding to all non-blocked nodes of the plurality of graphing nodes.

24. The method as defined in claim 22 wherein executing tasks corresponding to all blocked nodes of the plurality of graphing nodes further comprises repeating execution of tasks corresponding to all blocked nodes of the plurality of graphing nodes once data has become available.

25. The method as defined in claim 13 wherein when a task corresponding to a node of the plurality of graphing nodes has been completely computed, setting status of the node to dirty status until all asynchronous data has been loaded.

26. The method as defined in claim 13 wherein executing all dirty nodes of the plurality of graphing nodes in accordance with respectively assigned threading models further comprises: re-executing a task corresponding to a node of the plurality of graphing nodes, wherein the re-execution comprises:
    locating one or more predecessor nodes of the node;
    determining whether the one or more predecessor nodes are set to dirty status;
    reexecuting each task corresponding to the one or more predecessor nodes that are set to dirty status; and executing the task corresponding to the node of the plurality of graphing nodes.

27. The method as defined in claim 13 wherein assigning each node of the plurality of graphing nodes to one or more processing queues is accomplished by a scheduler.

28. The method as defined in claim 27 wherein assigning each node of the plurality of graphing nodes to one or more processing queues further comprises grouping tasks within queues by predecessor tasks.

29. The method as defined in claim 27 wherein assigning each node of the plurality of graphing nodes to one or more processing queues further comprises grouping tasks within queues by data sources.

30. The method as defined in claim 27 wherein assigning each node of the plurality of graphing nodes to one or more processing queues further comprises a weighted combination of:
grouping tasks within queues within queues by predecessor tasks; and
grouping tasks within queues within queues by data sources.

31. A system for optimizing data computed by multiple processors comprising:
a plurality of processors wherein:
the processors are respectively coupled to a plurality of cache memories; and
the processors are coupled to a common data bus;
a user interface comprising a user data entry interface and a display interface;
a memory for storing data and one or more instructions for execution by the plurality of processors to implement one or more functions of the data processing system to:
define a plurality of tasks requiring execution;
identify one or more dependencies for each respective task of the plurality of tasks, the one or more dependencies comprising at least one of a resource dependency and a memory dependency;
determine dependencies between for each respective task of the plurality of tasks wherein the dependencies include directional dependencies;
create a directed graph, wherein the directed graph includes:
a plurality of nodes, the nodes respectively corresponding to the plurality of tasks requiring execution; and
a plurality of directed edges that respectively correspond to the directional dependencies, each of said directed edges originating from a node of the plurality of nodes and terminating on another node of the plurality of nodes; and
analyze the directed graph to assign execution of tasks to a plurality of processors to maximize computational efficiency;
attribute a threading model to each node of the plurality of nodes;
assign a parallel threading model to each said node where said node corresponds to a task that is independent, may operate in parallel, and has a non-blocked status;
assign a strip-mine threading model to each node in a collection of nodes that correspond to tasks that operate on common data; and
assign a non-threading model is assigned to nodes corresponding to tasks that must be executed sequentially;
wherein a strip-mine threading model comprises:
partitioning a data set into a plurality of subsets, the size of each subset of the plurality of subsets chosen to be containable within a cache memory of predetermined size associated with a processor of the plurality of processors;
allocating processing of a subset of the plurality of subsets to the processor;
loading the subset of the plurality of subsets into the cache memory associated with the processor;
executing a task utilizing the subset of the plurality of subsets; and
indicating, by the processor, that another subset of the plurality of subsets may be allocated.

32. The system as defined in claim 31 wherein multiple threading models may be assigned to any node of said plurality of nodes.

33. The system as defined in claim 31 wherein the instructions to be executed by the plurality of processors further include instructions to assign a branch prediction model to a node of the plurality of nodes, the branch prediction model determined by an entropy characterization of data operated on by a function corresponding to the node.

34. The system as defined in claim 31 wherein the instructions to be executed by the plurality of processors further include instructions to assign each node of the plurality of nodes to one or more processing queues and execute tasks corresponding to each node assigned to the one or more processing queues.

35. The system as defined in claim 34, wherein each node of the plurality of nodes is assigned to one or more processing queues based on the an identified memory dependency identified for that node.

36. The system as defined in claim 35, wherein the memory dependency includes a desired cache level allocation.

37. The system as defined in claim 34 further comprising
for each node of the plurality of nodes, determining whether the status of each node is blocked or un-blocked; and
executing tasks corresponding to all non-blocked nodes of the plurality of nodes then executing tasks corresponding to all blocked nodes of the plurality of nodes.

38. The system as defined in claim 37, further comprising repeating execution of tasks corresponding to all blocked nodes of the plurality of graphing nodes once data has become available.

39. The system as defined in claim 31, wherein the instructions to be executed by the plurality of processors further include instructions to perform the following steps until all data is processed:
setting status of all nodes of the plurality of nodes to processed or unprocessed status;
when a task corresponding to a node of the plurality of nodes has been completely computed, setting status of the node to processed status;
when data corresponding to a node of the plurality of nodes has been changed, setting status of the node to unprocessed status; and
executing tasks corresponding to all unprocessed nodes of the plurality of nodes in accordance with respectively assigned threading models.

40. A system for optimizing data computed by multiple processors comprising:
a plurality of processors wherein:
the processors are respectively coupled to a plurality of cache memories: and
the processors are coupled to a common data bus;

a user interface comprising a user data entry interface and a display interface;
a memory for storing data and one or more instructions for execution by the plurality of processors to implement one or more functions of the data processing system to:
define a plurality of tasks requiring execution;
identify one or more dependencies for each respective task of the plurality of tasks, the one or more dependencies comprising at least one of a resource dependency and a memory dependency;
determine dependencies between for each respective task of the plurality of tasks wherein the dependencies include directional dependencies;
create a directed graph, wherein the directed graph includes:
a plurality of nodes, the nodes respectively corresponding to the plurality of tasks requiring execution; and
a plurality of directed edges that respectively correspond to the directional dependencies, each of said directed edges originating from a node of the plurality of nodes and terminating on another node of the plurality of nodes; and
analyze the directed graph to assign execution of tasks to a plurality of processors to maximize computational efficiency;
perform the following steps until all data is processed:
setting status of all nodes of the plurality of nodes to processed or unprocessed status;
when a task corresponding to a node of the plurality of nodes has been completely computed, setting status of the node to processed status;
when data corresponding to a node of the plurality of nodes has been changed, setting status of the node to unprocessed status; and
executing tasks corresponding to all unprocessed nodes of the plurality of nodes in accordance with respectively assigned threading models.

* * * * *